United States Patent [19]

Käshammer et al.

[11] Patent Number: 6,034,279
[45] Date of Patent: Mar. 7, 2000

[54] METHOD FOR THE PRODUCTION OF γ, δ-UNSATURATED KETONES BY REACTING TERTIARY ALLYL ALCOHOLS WITH ALKENYL ALKYL ETHERS

[75] Inventors: Stefan Käshammer; Detlef Ruff, both of Ludwigshafen, Germany

[73] Assignee: BASF Aktiengesellschaft, Ludwigshafen, Germany

[21] Appl. No.: 09/147,597

[22] PCT Filed: Nov. 18, 1997

[86] PCT No.: PCT/EP97/06425

§ 371 Date: Jan. 29, 1999

§ 102(e) Date: Jan. 29, 1999

[87] PCT Pub. No.: WO98/23570

PCT Pub. Date: Jun. 4, 1998

[30] Foreign Application Priority Data

Nov. 29, 1996 [DE] Germany .............. 196 49 564

[51] Int. Cl.[7] .................................. C07C 45/48
[52] U.S. Cl. .................. 568/391; 568/315; 568/317; 568/347; 568/349; 568/395
[58] Field of Search ................... 568/309, 322, 568/361, 383, 404, 405, 408, 315, 388, 395, 317, 347, 349, 391

[56] References Cited

U.S. PATENT DOCUMENTS 3,453,317  7/1969  Marbet et al. ............ 260/476
4,892,977  1/1990  Nieh ........................ 568/618
5,077,442  12/1991  Hara et al. ............... 568/864

FOREIGN PATENT DOCUMENTS 11 93 490  5/1965  Germany .

OTHER PUBLICATIONS

Houben–Weyl, "Methods in Organic Chemistry", 4th Edition, 1964, vol. 12,2 (pp. 143–376 for phosphoric esters).
Houben–Weyl, "Methods in Organic Chemistry", 4th Edition, 1964, vol. 12,1 (pp. 220–266 for the phosphinic acids).
Houben–Weyl, "Methods in Organic Chemistry", 4th Edition, 1964, vol. 12,1 (pp. 348–550 for the phosphonic acids).

*Primary Examiner*—Gary Geist
*Assistant Examiner*—Sreeni Padmanabhan
*Attorney, Agent, or Firm*—Oblon, Spivak, McClelland, Maier & Neustadt, P.C.

[57] ABSTRACT

An improved process is described for preparing γ,δ-unsaturated ke-tones, which are in demand as aroma substances and intermediates for vitamins and carotenoids, by reacting tertiary allyl alcohols and alkenyl alkyl ethers in the presence of acid catalysts at elevated temperature, which comprises carrying out the reaction in the presence of a phosphorus derivative of the formula IV

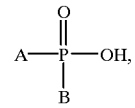

(IV)

where

A and B are each a branched or unbranched alkyl or alkoxy having from 1 to 10 carbons, a substituted or unsubstituted aryl, cycloalkyl, aryloxy or cycloaryloxy;

A can additionally be —H or —OH or

A and B together are a substituted or unsubstituted tetramethylene or pentamethylene or substituted or unsubstituted phenyl-1,2-diol or 1,1'-binaphthyl-2,2'-diol.

12 Claims, No Drawings

METHOD FOR THE PRODUCTION OF γ,δ-UNSATURATED KETONES BY REACTING TERTIARY ALLYL ALCOHOLS WITH ALKENYL ALKYL ETHERS

This is the U.S. National Stage Application of PCT/EP97/06425 filed Nov. 18, 1997 now WO 98/23570 published Jun. 4, 1998.

1. Subject-matter of the invention

The present invention relates to improvements in a process for preparing γ,δ-unsaturated ketones by a Carroll reaction.

A number of γ,δ-unsaturated ketones have proved to be valuable aroma substances and to be intermediates for producing vitamins E and $K_1$ and carotenoids.

2. Prior art

DE 1 193 490 discloses a process for preparing γ,δ-unsaturated ke-tones by reacting a tertiary alcohol with enol ethers in the presence of an acid catalyst at elevated temperature. A particularly suitable acid catalyst mentioned here is phosphoric acid. The reaction times required to achieve complete conversion of the tertiary allyl alcohol are from 13 to 18 hours at from 125 to 140° C., a pressure of approximately 10 bar and a phosphoric acid concentration of from 0.1 to 0.2% by weight. A disadvantage of this method is the long reaction times which, in an industrial process, give rise to large reaction volumes and thus high capital expenditure.

The conventional way of accelerating chemical reactions is to increase the reaction temperatures and/or to increase the amount of catalyst. If this is attempted in the reactions described in DE 1 193 490, the yields of γ,δ-unsaturated ketones decrease, so that an industrial process is no longer economical (see comparative examples 1–3).

3. OBJECT OF THE INVENTION

It is an object of the present invention to decrease the reaction times of the reaction of tertiary allyl alcohols with alkenyl ethers without impairing the yield.

4. SUMMARY OF THE INVENTION

We have found that this object is achieved, surprisingly, by special phosphorus derivatives which catalyze the reaction of tertiary allyl alcohols with alkenyl ethers very selectively at comparatively short reaction times.

The present invention therefore relates to a process for preparing γ,δ-unsaturated ketones of the formula I

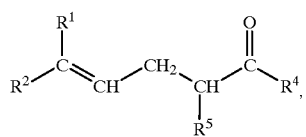

(I)

where
$R^1$ and $R^2$ are each a saturated or unsaturated branched or unbranched alkyl, an aryl or an alkylaryl, each of which is unsubstituted or substituted by an oxygen-containing group
or else
$R^1$ and $R^2$ together are a tetramethylene or pentamethylene, each of which may be substituted by one or more lower alkyls, $R^4$ is a $C_1$–$C_4$-alkyl and
$R^5$ is hydrogen or a $C_1$–$C_4$-alkyl, by reacting a tertiary allyl alcohol of the formula II

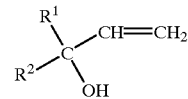

(II)

with an alkenyl alkyl ether of the formula III

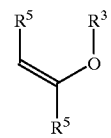

(III)

where $R^3$ is a $C_1$–$C_4$-alkyl, preferably a methyl, and
$R^4$ and $R^5$ have the meaning specified above,
at temperatures of from 100 to 200° C. in the presence of an acid catalyst, which comprises carrying out the reaction in the presence of a phosphorus derivative of the formula IV

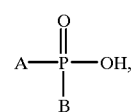

(IV)

where
A and B are each a branched or unbranched alkyl or alkoxy having from 1 to 10 carbons, an aryl, cycloalkyl, aryloxy or cycloalkyloxy, each of which may be substituted by one or more $C_1$–$C_4$-alkyl or alkoxy groups, OH groups or halogen;
A can additionally be —H or —OH or
A and B together are a tetramethylene or pentamethylene, each of which may be substituted by one or more alkyls having 1 or 2 carbons, or together are a substituted or unsubstituted 1,2-phenyl-diol or a substituted or unsubstituted 1,1'-binaphthyl-2,2'-diol.

The process according to the invention is particularly successful if the tertiary allyl alcohol of the formula II is reacted with the alkenyl alkyl ether of the formula III in the presence of phosphorus-containing aryl or aryloxy derivatives. Examples are, in particular, phenylphosphonic acid, diphenylphosphinic acid, phenyl phosphate and diphenyl phosphate. On an industrial scale, a mixture of phenyl phosphate and diphenyl phosphate is generally used, as obtained simply and cheaply in the reaction of phenol with $POCl_3$ and subsequent hydrolysis.

The catalysts claimed for the process according to the invention may be readily synthesized on a preparative scale using standard methods (cf. Houben-Weyl, "Methoden der Organischen Chemie" [Methods in organic chemistry], 4th edition, 1964, Volume 12,2, pages 143 to 376 for phosphoric esters; volume 12,1, pages 220 to 266 for the phosphinic acids and volume 12,1, pages 348 to 550 for the phosphonic acids).

They are generally used in a concentration of from 0.0001 mol to 1 mol, preferably from 0.001 mol to 0.05 mol, of catalyst per kg of reaction mixture. They may be used in the from of a solid, a melt or else in the form of a solution. Catalyst is added either continuously or a little at a time.

Specific examples of solvents for the catalyst are water, acetone, methanol, dimethyl sulfoxide or toluene. However, it is also possible to use the tertiary allyl alcohol of the formula II used as starting material as solvent for the catalysts.

Tertiary allyl alcohols of the formula II which are preferably used are those where $R^1$ is a saturated or unsaturated branched or unbranched alkyl, an aryl or an alkyl aryl, $R^2$ is a $C_1$–$C_4$-alkyl, in particular a methyl, or else $R^1$ and $R^2$ together are a tetramethylene or pentamethylene, each of which may be substituted by one or more lower alkyl groups.

Specific examples are, in particular, 3-methyl-1-buten-3-ol, hydrolinalool (3,7-dimethyl-1-octen-3-ol), 1-vinylcyclohexanol, nerolidol (3,7,11-trimethyldodeca-1,6,10-trien-3-ol), linalool (3,7-dimethylocta-2,6-dien-3-ol), hydronerolidol (3,7,11-trimethyldodeca-1,6-dien-3-ol) and tetrahydronerolidol (3,7,11-trimethyldodecan-3-ol).

Alkenyl alkyl ethers of the formula III which are preferably used are those where $R^3$ is a methyl or ethyl and $R^4$ is hydrogen or a methyl and $R^5$ is a methyl.

Specific examples of suitable alkenyl alkyl ethers are: isopropenyl methyl ether, isopropenyl ethyl ether, isopropenyl propyl ether, isopropenyl butyl ether, isopropenyl isobutyl ether, 2-methoxy-1-butene, 2-ethoxy-1-butene, 2-propoxy-1-butene, 2-butoxy-1-butene, 2-methoxy-2-butene, 2-ethoxy-2-butene, 2-methoxy-1-pentene, 2-ethoxy-1-pentene, 2-methoxy-2-pentene, 2-ethoxy-2-pentene, 3-methoxy-2-pentene and 3-ethoxy-2-pentene, in particular isopropenyl methyl ether.

On an industrial scale, isopropenyl methyl ether is frequently employed in the form of an azeotrope of isopropenyl methyl ether and methanol, as is produced in the preparation by thermocleavage of dimethoxypropane, since no significant losses of yield occur in this case and the complex removal of methanol from the azeotrope can be omitted.

The molar ratio of tertiary allyl alcohol of the formula II to the alkenyl alkyl ether of the formula III in the process according to the invention is generally from 1:2.0 to 1:5.0, preferably from 1:2.1 to 1:3.0.

The reaction is generally carried out at from 100 to 200° C., preferably at from 100 to 170° C., in particular at from 130 to 160° C., in a pressure vessel, under the pressure which is established at the reaction temperatures. When the upper temperature region is employed, it is advisable to add further catalyst in the course of the reaction, since this decomposes fairly slowly at relatively high temperatures.

To carry out the process, a procedure is generally followed such that either a mixture of the tertiary allyl alcohol and the alkenyl alkyl ether is introduced into the reaction vessel and, after heating the mixture to the reaction temperature, the catalyst is added either continuously or a little at a time in the form of a solid, a melt or, in particular, dissolved in a suitable solvent, or else only the alkenyl alkyl ether, with or without a portion of the allyl alcohol, is introduced and, after it is heated, a mixture or a solution of the catalyst of the formula IV and the tertiary alcohol, or, respectively, in the tertiary alcohol, is added either continuously or a little at a time.

The reaction time is generally from 6 to 10 hours, preferably from 7 to 9 hours.

The reaction can be performed batchwise or continuously.

On an industrial scale, the reaction is generally carried out continuously.

The reaction vessels used are then a cascade of stirred tanks or tubes designed for reactions under pressure, or a cascade or appropriate stirred tanks and tubes.

To work-up the reaction mixture, it is generally distilled, if appropriate after neutralization or buffering. The only important factor here is that the mixture to be distilled is not basic, or at least is only weakly basic.

Using the process according to the invention, the γ,δ-unsaturated ketones of the formula I, which are in demand as aroma substances and as intermediates for vitamins and carotenoids, can be prepared in very good yields and in comparatively short reaction times.

EXAMPLES 1 TO 10

A pressure vessel of corrosion-resistant material (HC4 steel) having a volume of 300 ml was charged with the amount given in Table 1 of the tertiary allyl alcohol specified in Table 1 and the amount given in Table 1 of an isopropenyl methyl ether/methanol azeotrope (IMA) containing approximately 9% by weight of methanol and the amount given in Table 1 of the catalyst specified in Table 1, the pressure vessel was closed, flushed with nitrogen and then heated over the course of 30 minutes (min) to the reaction temperature given in Table 1. After the reaction time given in Table 1, the contents of the pressure vessel were emptied and, if appropriate after neutralization or buffering, distilled. The yields of unsaturated ketone achieved were determined by gas chromatography (GC) against an internal standard and are reported in Table 1.

TABLE 1

| Example | Allyl alcohol [g] | IMA [g] | Catalyst [g] | Reaction temperature [° C.] | Reaction time [h] | Yield of reaction product [% of theory] |
|---|---|---|---|---|---|---|
| 1 | 3-Methyl-1-buten-3-ol 34 | 96 | Diphenyl phosphate 0.168 | 125 | 8 | 6-Methyl-5-hepten-2-one 86* |
| 2 | Hydrolinalool 59 | 85 | 1-Naphthyl phosphate 0.164 | 150 | 8 | Hydrogeranylacetone 82 |
| 3 | Hydrolinalool 60 | 89 | Diphenyl phosphate 0.189 | 125 | 8 | Hydrogeranylacetone 88 |
| 4 | 1-Vinylcyclohexanol 51 | 97 | Mono-(p-tert-butylphenyl) phosphate 0.180 | 135 | 8 | 4-Cyclohexylidenbutan-2-one 74* |

TABLE 1-continued

| Example | Allyl alcohol [g] | IMA [g] | Catalyst [g] | Reaction temperature [° C.] | Reaction time [h] | Yield of reaction product [% of theory] |
|---|---|---|---|---|---|---|
| 5 | Nerolidol 66 | 68 | Mono-(o-chlorophenyl) phosphate 0.133 | 150 | 7 | Farnesylacetone 88** |
| 6 | Linalool 47 | 72 | Monophenyl phosphate/Diphenyl phosphate (58:4.0) 0.072 | 150 | 8 | Geranylacetone 88** |
| 7 | Linalool 47 | 72 | Mono-(o-hydroxyphenyl) phosphate 0.106 | 150 | 8 | Geranylacetone 85** |
| 8 | Hydronerolidol 66 | 63 | Diphenylphosphinic acid 0.851 | 150 | 10 | Hydrofarnesylacetone 87*** |
| 9 | Hydronerolidol 71 | 71 | 1,1'-Binaphthyl-2,2'-diyl hydrogen phosphate 0.1128 | 150 | 6 | Hydrofarnesylacetone 83 |
| 10 | Tetrahydronerolidol 68 | 71 | Diphenyl phosphate 0.0774 | 150 | 8 | Tetrahydrofarnesylacetone 93 |

*After distillation using a Vigreux column under reduced pressure
**After buffering with sodium acetate and distillation using a Vigreux column under reduced pressure
***After neutralization with aluminum triisopropoxide and distillation using a Vigreux column under reduced pressure Example 11

393 g of hydrolinalool and 1187 g of an IMA mixture were introduced into a 4 l pressure vessel. The pressure vessel was flushed with nitrogen and heated to 150° C. Over the course of 4 h, a further 393 g of hydrolinalool and a solution of 1.5 g of diphenyl phosphate in 25 ml of acetone were introduced into the pressure vessel by means of two pumps. The reaction temperature during this was 150° C. The contents of the pressure vessel were then stirred for a further 2 h at 150° C. 400 g of the reactor discharge were neutralized with 0.126 g of aluminum sec-butoxide and distilled using a Vigreux column at 0.9 mbar. The yield of hydrogeranylacetone was 92%, based on hydrolinalool used.

Example 12

71 g of an IMA mixture were charged into a pressure vessel having a volume of approximately 300 ml. The pressure vessel was closed, flushed with nitrogen and heated to 135° C. A solution of 133 mg of mono-(p-tert-butylphenyl) phosphate in 38 g of 1-vinylcyclohexanol was added over the course of 4 h in 8 equal portions every half hour using a pump. The contents of the pressure vessel were then stirred for a further 4 h at 135° C. to complete the reaction.

The reaction discharge was admixed with 54 mg of sodium acetate and distilled. The yield of 4-cyclohexylidenebutane-2-one was 82%.

Example 13

72 g of an IMA mixture were charged into a pressure vessel having a volume of approximately 300 ml. The pressure vessel was closed, flushed with nitrogen and heated to 150° C. A solution of 72 mg of a mixture comprising monophenyl phosphate and diphenyl phosphate in a molar ratio of 58:40, dissolved in 47 g of linalool, was added over the course of 4 h in 8 equal portions every half hour using a pump. The contents of the pressure vessel were then stirred for a further 3 h at 150° C. to complete the reaction.

The reaction discharge was admixed with 36 mg of sodium acetate and distilled. The yield of geranylacetone was 88%.

Example 14

72 g of an IMA mixture were introduced into a pressure vessel having a volume of approximately 300 ml. The pressure vessel was closed, flushed with nitrogen and heated to 160° C. A solution of 121 mg of mono-(p-methoxyphenyl) phosphate, dissolved in 47 g of linalool, was added over the course of 4 h in 8 equal portions every half hour using a pump. The contents of the pressure vessel were then stirred for a further 4 h at 160° C. to complete the reaction.

The reaction discharge was admixed with 60 mg of sodium acetate and distilled. The yield of geranylacetone was 89%.

Example 15

603 g of hydronerolidol and 1140 g of an IMA mixture were introduced into a 4 l pressure vessel. The pressure vessel was flushed with nitrogen and heated to 150° C. Over the course of 5 h, a further 603 g of hydrolinalool and a solution of 11 g of phenylphosphonic acid in 50 ml of acetone were introduced into the pressure vessel by means of two pumps. The reaction temperature during this was 150° C. The contents of the pressure vessel were then stirred for a further 5 h at 150° C.

100 g of the reactor discharge were neutralized with 61 g of a 1% strength aluminum triisopropoxide solution in toluene and distilled using a Vigreux column at 0.4 mbar. The yield of hydrofarnesylacetone was 88%, based on hydronerolidol.

Example 16

476 g of hydronerolidol and 986 g of an IMA mixture were introduced into a 4 l pressure vessel. The pressure vessel was flushed with nitrogen and heated to 125° C. Over the course of 5 h, a further 476 g of hydrolinalool and a solution of 2.5 g of diphenyl phosphate in 25 ml of acetone were introduced into the pressure vessel by means of two pumps. The reaction temperature during this was 125° C. The contents of the pressure vessel were then stirred for a further 3 h at 125° C.

The yield of hydrofarnesylacetone was 87%, based on hydronerolidol used.

Comparative Examples 1 to 3

0.4 mol of the respective tertiary allyl alcohol given in Table 2, 2.3 equivalents of isopropenyl methyl ether and sufficient phosphoric acid to achieve the $H_3PO_4$ concentration in the reaction mixture specified in Table 2 were introduced into the pressure vessel described in Example 1, the pressure vessel was closed, flushed with $N_2$ and then heated in the course of 30 min to the reaction temperature specified in Table 2, column 4, a pressure of approximately 10 bar being produced, which decreased in the course of the reaction.

After the reaction time specified in Table 2, column 4, the reaction was complete. The pressure vessel was cooled and opened. The reaction mixture was buffered with sodium acetate. Low-boiling constituents were subsequently distilled off at atmospheric pressure and then the unsaturated γ,δ-ketone was distilled off at 1 to 2 mbar. The yields achieved at higher temperatures and shorter reaction times (cf. column 4) are compared in Table 2 with those achieved according to Examples 1, 10 and 12 of DE 11 93 490 (cf. column 5).

TABLE 2

| 1 Comparative Example | 2 Tertiary allyl alcohol | 3 $H_3PO_4$ concentration [% by weight] | 4 Ketone yield at higher reaction temperatures and shorter times [% of theory] | 5 Ketone yield according to DE 11 93 490 [% of theory] |
|---|---|---|---|---|
| 1 | 3-Methyl-1-buten-3-ol | 0.15 | 75 (8 h at 150° C.) | 93* (13–15 h at 125° C.) |
| 2 | Dihydrolinalool | 0.13 | 79 (4 h at 175° C.) | 83** (14 h at 125° C.) |
| 3 | Nerolidol | 0.13 | 74 (8 h at 125° C.) | 87*** (16 h at 125° C.) |

*cf. Example 1 of DE 11 93 490
**cf. Example 10 of DE 11 93 490
***cf. Example 12 of DE 11 93 490

We claim:

1. A process for preparing γ,δ-unsaturated ketones of the formula I

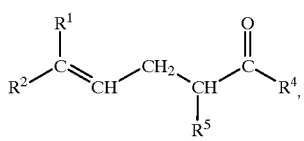

(I)

where $R^1$ and $R^2$ are each a saturated or unsaturated branched or unbranched alkyl, an aryl or an alkylaryl, each of which is unsubstituted or substituted by an oxygen-containing group, or else $R^1$ and $R^2$ together are a tetramethylene or pentamethylene, each of which may be substituted by one or more lower alkyls, $R^4$ is a $C_1$–$C_4$-alkyl and
$R^5$ is hydrogen or a $C_1$–$C_4$-alkyl,
by reacting a tertiary allyl alcohol of the formula II

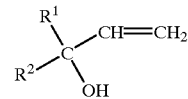

(II)

with an alkenyl alkyl ether of the formula III

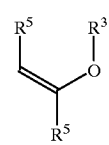

(III)

where $R^3$ is a $C_1$–$C_4$-alkyl, at temperatures of from 100 to 200° C. in the presence of an acid catalyst, which comprises carrying out the reaction in the presence of a phosphorus derivative of the formula IV

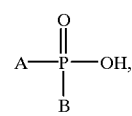

(IV)

where

A and B are each a branched or unbranched alkyl or alkoxy having from 1 to 10 carbons, an aryl, cycloalkyl, aryloxy or cycloalkyloxy, each of which may be substituted by one or more $C_1$–$C_4$-alkyl or alkoxy groups, OH groups or halogen;

A can additionally be —H or —OH or

A and B together are a tetramethylene or pentamethylene, each of which may be substituted by one or more alkyls having 1 or 2 carbons, or together are a substituted or unsubstituted 1,2-phenyl-diol or a substituted or unsubstituted 1,1'-binaphthyl-2,2'-diol.

2. A process as claimed in claim 1, wherein the tertiary alcohol of the formula II is reacted with the alkenyl alkyl ether of the formula III in the presence of phenylphosphonic or diphenylphosphinic acid, phenyl phosphate, diphenyl phosphate or a mixture of phenyl phosphate and diphenyl phosphate, or phenylphosphonic acid and diphenylphosphonic acid respectively.

3. A process as claimed in claim 1, wherein the catalyst concentration in the reaction mixture is from 0.0001 mol to 1 mol of catalyst per kg of reaction mixture.

4. A process as claimed in claim 1, wherein the catalyst is introduced into the reaction mixture as solid, as melt or dissolved in a suitable solvent.

5. A process as claimed in claim 1, wherein the catalyst is introduced into the reaction mixture dissolved in tertiary allyl alcohol of the formula II.

6. A process as claimed in claim 1, wherein the reaction is carried out at from 100 to 170° C. in a closed reaction vessel.

7. A process as claimed in claim 1, wherein the tertiary allyl alcohol of the formula II and the alkenyl alkyl ether of the formula III are used in a molar ratio of from 1:2.0 to 1:5.0.

8. A process as claimed in claim 1, wherein the tertiary allyl alcohol of the formula II used is 3-methyl-1-buten-3-ol, linalool, hydrolinalool, nerolidol, hydronerolidol, tetrahydronerolidol or 1-vinylcyclohexanol.

9. A process as claimed in claim 1, wherein the alkenyl alkyl ether of the formula III used is isopropenyl methyl ether in the form of the azeotropic mixture of isopropenyl methyl ether and methanol.

10. A process as claimed in claim 1, wherein the process is carried out continuously in a cascade of closed stirred tanks or tubes or else a cascade of closed stirred tanks and tubes.

11. The process of claime 1, wherein $R^3$ is $C_1$ alkyl.

12. The process of claim 7, wherein said molar ratio is from 1:2.1 to 1:3.0.

* * * * *